US006518440B2

(12) United States Patent
Lightner

(10) Patent No.: US 6,518,440 B2
(45) Date of Patent: Feb. 11, 2003

(54) HYDROXYMETHYLFURFURAL DERIVED FROM CELLULOSE CONTAINED IN LIGNOCELLULOSE SOLIDS

(76) Inventor: Gene E. Lightner, 706 SW. 296, Federal Way, WA (US) 98023

( * ) Notice: Subject to any disclaimer, the term of this patent is extended or adjusted under 35 U.S.C. 154(b) by 184 days.

(21) Appl. No.: 09/800,557

(22) Filed: Mar. 5, 2001

(65) Prior Publication Data

US 2002/0123636 A1 Sep. 5, 2002

(51) Int. Cl.[7] ............................................. C07D 307/02
(52) U.S. Cl. ...................................... 549/497
(58) Field of Search ......................................... 549/497

(56) References Cited

PUBLICATIONS

Organic Chemistry, 1943, Hill and Kelly, p. 466, p. 480.
Unit Operations, 1950, G.G. Brown Et. al., pp. 542–543, p. 548.

Primary Examiner—Amelia Owens

(57) ABSTRACT

A method to produce hydroxymethylfurfural from cellulose contained within lignocellulose solids is disclosed. Hemicellulose contained in lignocellulose solids is converted to furfural. Lignocellulose solids, containing cellulose, is added to a vessel containing an aqueous acidic solution which is employed for hydrolysis of cellulose, contained within lignocellulose solids, to form glucose. Subjecting the glucose to additional hydrolysis to convert glucose and form hydroxymethylfurfural and removing hydroxymethylfurfural from the vessel are procedures applied. Solids remaining from hydrolysis containing lignins are filtered and then extracted with water to remove aqueous acidic solution contained within solids and form an extractate containing dilute aqueous acidic solution. The extactate is combined with a dilute solution of aqueous acidic solution removed from the vessel. Dilute solutions of aqueous acidic solution are treated to remove water and then the aqueous acidic solution is recycled to the vessel employed for hydrolysis of cellulose within lignocellulose solids.

17 Claims, 2 Drawing Sheets

HYDROXYMETHYLFURFURAL DERIVED FROM CELLULOSE CONTAINED IN LIGNOCELLULOSE SOLIDS

BACKGROUND OF THE INVENTION

Glucose and xylose, derived from lignocellulose solids in the prior art, is customarily fermented to produce ethanol. Lignocellulose solids are selected from the group consisting of wood, waste paper and municipal solid waste including an individual or a combination including an individual or a combination thereof Hemicellulose, contained within lignocellulose solids, by hydrolysis in a first stage forms xylose which can be fermented to form ethanol. Xylose, within the first stage, upon additional reaction forms volatile furfural and lignocellulose solids containing cellulose and lignins substantially free of hemicellulose. The volatile furfural and water forms a vapor which is removed from the first stage. Hydrolysis of cellulose, contained in the lignocellulose solids, by a second stage, glucose is formed. Upon additional reaction of glucose hydroxymethylfurfural is formed. Fermentation of the mire containing glucose and hydroxymethylfurfural regards hydroxymethylfurfural as an unwanted constituent in the glucose mixture for fermentation. Hydroxymethylfurfural cannot be fermented to form ethanol by any known fermentation procedure.

It is therefore an object of this invention to obviate many of the limitations or disadvantages of the prior art.

The present concern is about producing hydroxymethylfurfural from lignocellulose solids containing cellulose.

A distinct object of this invention is to subject cellulose, contained in lignocellulose solids, to hydrolysis of the cellulose to form glucose and inevitably form hydroxymethylfurfural.

A crucial object of this invention is to remove hydroxymethylfurfural from solids containing lignins remaining from hydrolysis.

Another object of this invention is to avert fermentation of glucose and hydroxymethylfurfural.

Still another object of this invention is to extract solids, remaining from hydrolysis, to produce solids substantially free of acidic mixtures employed in hydrolysis. With the above and other objects in view, this invention relates to the novel features and alternatives and combinations presently described in the brief description of the invention.

APPLICATIONS OF THE INVENTION

A principle, applied in the present invention, employs acidic hydrolysis of hemicellulose and cellulose contained in lignocellulose solids. Hydrolysis of hemicellulose forms pentoses of several isomers. Upon dehydration reaction all pentoses form volatile furfural by the chemical formula, $C_5H_{10}O_5 = C_5H_4O_2 + 3H_2O$. Accordingly furfural is formed from pentoses derived from hemicellulose by hydrolysis. This chemical reaction is provided in Organic Chemistry, 1948, authored by Hill and Kelley, page 466.

Hydrolysis of cellulose contained in lignocellulose solids forms glucose. Upon dehydration reaction glucose forms volatile hydroxymethylfurfural by the chemical formula, $C_6H_{12}O_6 = C_6H_6O_3 + 3H_2O$. This chemical reaction is implied in Organic Chemistry, op. cit., page 480. Accordingly hydroxymethylfurfural is formed from glucose derived from cellulose by hydrolysis. HMF is the customary abbreviation for hydroxymethylfurfural Aqueous acidic solution employed for hydrolysis becomes diluted from water, upon dehydration to form furfural and HMF from sugars. Upon separation of diluted aqueous acidic solution, furfural, and HMF from hydrolysis surroundings, the diluted aqueous acidic solution can have water removed by miscellaneous methods, including vaporization. Conceivably the method of humidifying air with water to remove water from the diluted aqueous acidic solution is one such method. The method of humidifying air with water, disclosed by Brown, et. al, in Unit Operations, 1950, pages 542–543 and page 548, is a method for removing water by transferring water to air and accordingly humidifying air.

BRIEF DESCRIPTION OF THE INVENTION

The present invention, in its broadest aspect, is a method to produce hydroxymethylfurfural by providing lignocellulose solids containing lignins, hemicellulose and cellulose to a vessel for hydrolysis. Hemicellulose, contained in the lignocellulose solids, is hydrolyzed to form pentoses which are converted to furfural and water.

Cellulose, contained in the lignocellulose solids, is subjected to hydrolysis to produce glucose from hydrolysis of cellulose. Upon continued exposure to hydrolysis the glucose is converted to hydroxymethylfurfural and water. Solids, remaining from hydrolysis, are removed from the vessel employed for hydrolysis and are filtered to produce a filtrate containing an aqueous acidic solution for reuse for hydrolysis. The filtered solids are extracted with water to remove aqueous acidic solution and form an extractate containing dilute aqueous acidic solution. Hydroxymethylfurfural, furfural and dilute aqueous acidic solution contained in the vessel employed for hydrolysis, is removed from the vessel followed by separation of the dilute aqueous acidic solution. Dilute solution of aqueous acidic solution is combined with the extactate and is treated to remove water from the aqueous acidic solution and then the aqueous acidic solution is recycled to the vessel for employment of hydrolysis. Thus hydroxymethylfurfural and furfural and separated from aqueous acidic solution to become liquid fuels derived from lignocellulose solids.

Characteristics of the invention include;

Production of furfural from hemicellulose contained in lignocellulose solids.

Production of hydroxymethylfurfural from cellulose contained in lignocellulose solids.

Removal of lignocellulose solids, containing lignins, from the vessel utilized for hydrolysis.

Filtering removed solids containing lignins.

Filtered solids are extracted by water to produce solids substantially free of aqueous acidic solution.

Extractate contains aqueous acidic solution and is recycled to be utilized for hydrolysis.

Liquid fuels are derived from lignocellulose solids without fermentation.

BRIEF DESCRIPTION OF THE DRAWINGS

The features that are considered characteristic of this invention are set forth in the appended claims. This invention, however, both as to its origination and method of operations as well as additional advantages will best be understood from the following description when read in conjunction with the accompanying drawings in which:

DETAILED DESCRIPTION OF THE PREFERRED EMBODIMENT

Figure 1:
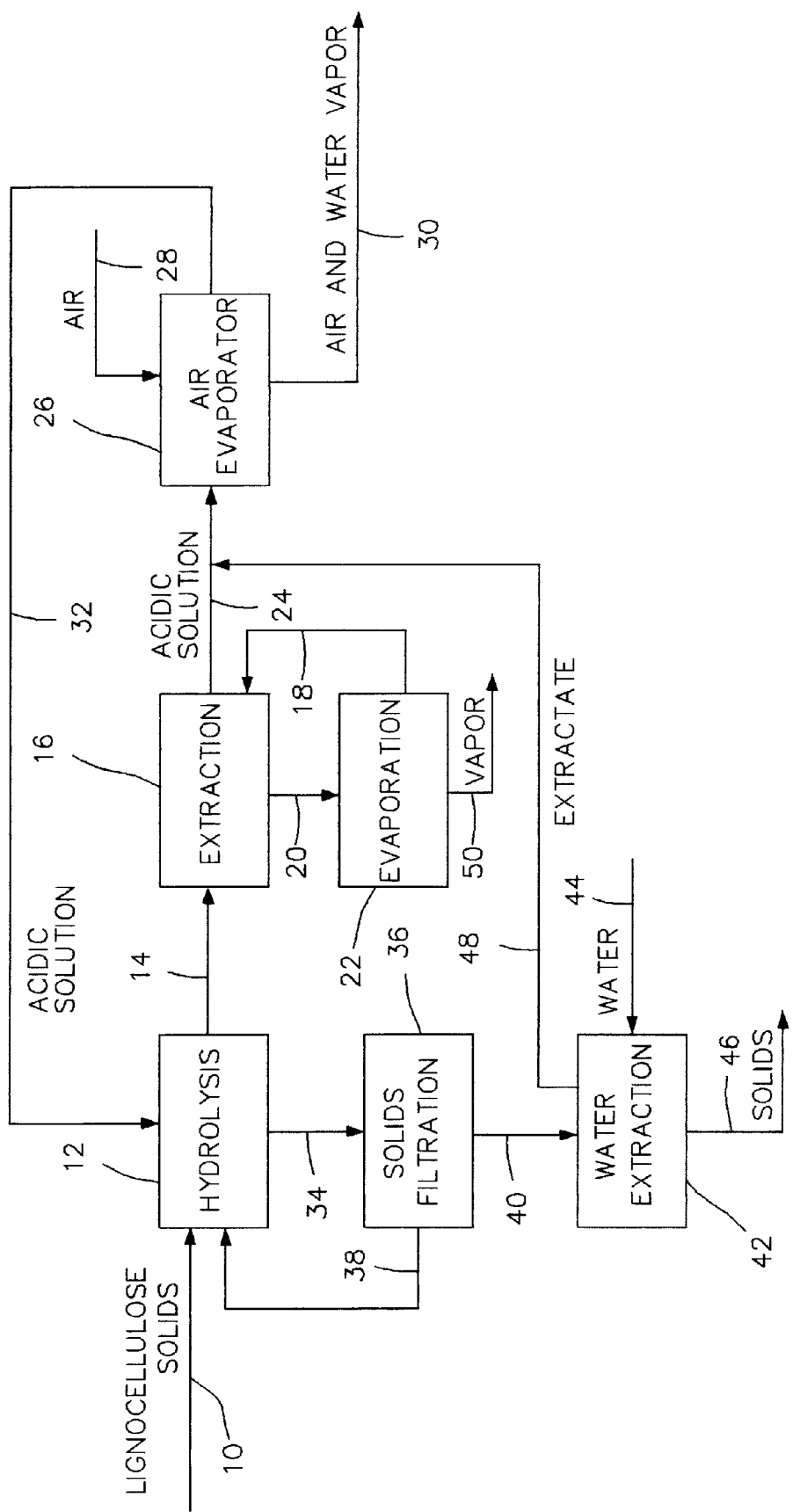
FIG. 1 is a flow sheet denoting the invention as set forth in the appended claims.

The flow diagram of FIG. 1 illustrates the general preferred embodiment of the present invention. In the diagram, rectangles represent stages, operations or functions of the present invention and not necessarily separate components. Details within each stage, operations or functions are not shown. Arrows indicate direction of flow of material in the method.

Referring to FIG. 1, a preferred method to hydrolyze lignocellulose solids to form furfural and hydroxymethylfurfural is depicted. Lignocellulose solids 10, added to hydrolysis stage 12. Upon hydrolysis, a solution containing furfural, hydroxymethylfurfural and an aqueous acidic solution used for hydrolysis 14 and is removed from hydrolysis stage 12 and transferred to extraction stage 16. Extraction stage 16 is supplied by solvent 18 to extract and dissolve furfural and hydroxymethylfurfural formed by hydrolysis 20 and a raffinate of an aqueous acidic solution 24. Dissolved furfural and hydroxymethylfurfural 20 is transferred to evaporation stage 22 to result in solvent 18 for recycle to extraction stage 16 and create vapor 50. Aqueous acidic solution 24 is conveyed to air evaporation stage 26 subjected to humidification by air 28 to create humidified air and water vapor 30 resulting in an acidic solution 32 recycled to hydrolysis stage 12. Solids 34, removed from hydrolysis stage 12, are conveyed to solids filtration stage 36 be filtered to produce filtrate 38 to be returned to hydrolysis stage 12. Filtered solids 40 are conveyed to water extraction stage 42 to be extracted by water 44 to produce extracted solids 46 and an extractate 48 combined with acidic solution 24. Aqueous acidic solution 24 has been diluted by water of dehydration of pentoses and glucose, produced by hydrolysis within the aqueous acidic solution, to form furfural and hydroxymethylfurfural. Diluted aqueous acidic solution 24, combined with extractate 48, is reconstituted, by removal of water, and then the reconstituted aqueous acidic solution is recycled. Solids 46, extracted with water, contain lignins and cellulose remaining from hydrolysis and are substantially free of the aqueous acidic solution. Vapor 50 contains furfural and hydroxymethylfurfural and is generally condensed to form a liquid. Solvent 18 must be soluble in furfural and hydroxymethylfurfural but insoluble in the aqueous acidic solution. Solvent 18 must be capable of dissolving hydroxymethylurfural. Solvent 18 must be substantially free of furfural and hydroxymethylfurfural when subjected to evaporation. A solvent with boiling point greater than the boiling points of furfural and hydroxymethylfurfural is necessary. Aqueous acidic solution 24 regularly contains sulfuric acid.

Figure 2:
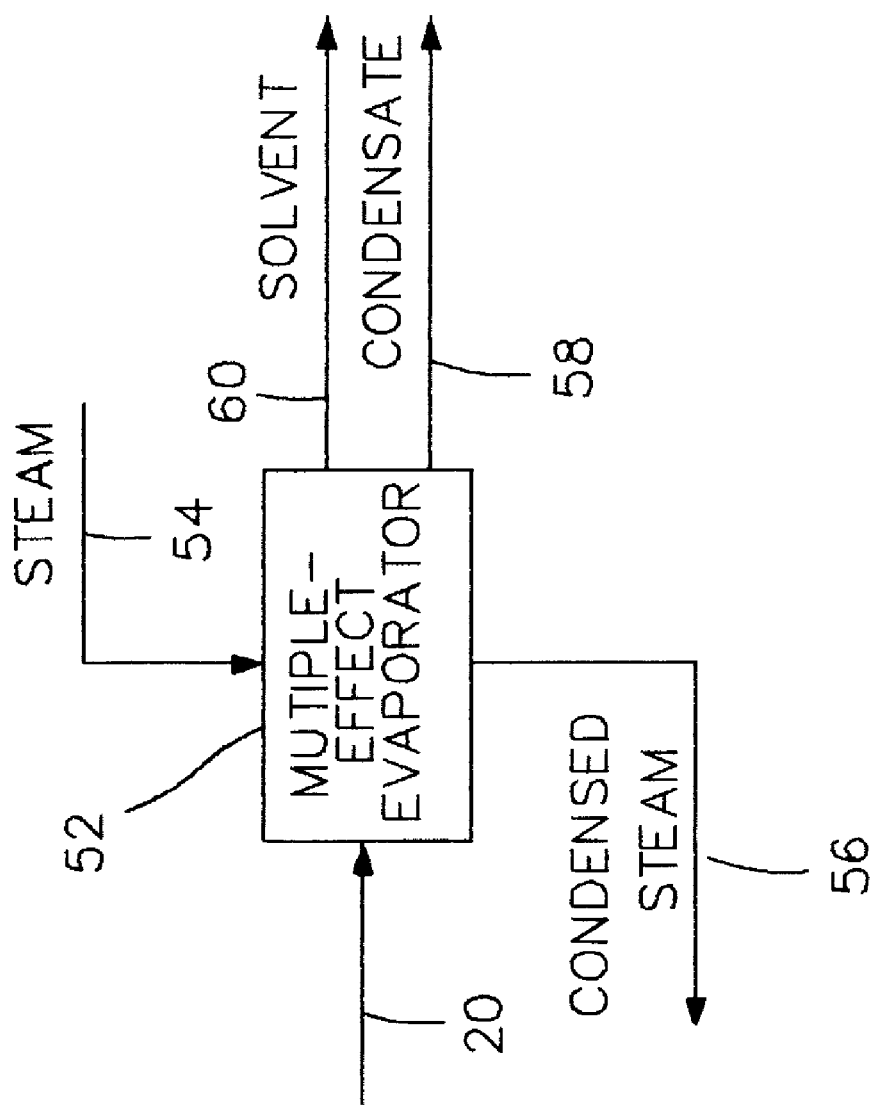
FIG. 2 is a flow sheet denoting a method to recover solvent containing dissolved HMF.

Referring to FIG. 2, liquid containing solvent, furfural and hydroxymethylfurfural 20 is conveyed to multiple-effect evaporation stage 52 heated by steam 54 which is condensed 56 to provide heat energy to multiple-effect evaporator 52. The multiple-effect evaporator 52 produces a condensate 58 of furfural and hydroxymethylfurfural and a raffinate 60 containing solvent. Operation of the multiple-effect evaporator 52 includes heat exchange tubes to receive vapor and produce condensate. Accordingly steam is applied to the first effect to provide vapor and a condensate of condensed water and provide an organic vapor. Organic vapor from the first effect provides vapor to the second effect heat exchange tubes and is condensed and so on to the remaining effects. Condensed vapor from each effect, excluding the first effect is combined to form a condensate 58 of furfural and hydroxymethylfurfural. Raffinate from each effect is combined to form a raffinate of solvent 60. Consequently energy to vaporize furfural and hydroxymethylurfural is substantially divided by the number of effects. This procedure when accomplished will furnish a combined raffinate to provide a solvent for extraction.

What is claimed is:

1. A method to convert cellulose contained within lignocellulose solids to form hydroxymethylurfural which comprises:

providing lignocellulose solids containing cellulose, and providing a vessel containing an aqueous acidic solution, and adding said lignocellulose solids to said vessel, and subjecting cellulose contained within said lignocellulose solids to hydrolysis by said aqueous acidic solution to form glucose, and subjecting said glucose to form hydroxymethylurfural, and removing said hydroxymethylurfural from said vessel, and separating solids, remaining from hydrolysis, from said vessel thereby producing hydroxymethylurfural from cellulose contained within lignocellulose solids and separating solids remaining from hydrolysis from the vessel.

2. The method of claim 1 wherein said lignocellulose solids contains hemicellulose are subjected to hydrolysis to form furfural.

3. The method of claim 1 wherein said hydroxymethylurfural is combined with furfural and aqueous acidic solution and removed from said vessel.

4. The method of claim 3 wherein previously removed hydroxymethylurfural containing furfural and aqueous acidic solution is extracted by a solvent capable of dissolving hydroxymethylurfural to form an extractate containing dissolved hydroxymethylfurfural and furfural separated from aqueous acidic solution.

5. The method of claim 4 wherein said extractate containing dissolved hydroxymethylurfural and furfural is subjected to evaporation to substantially separate hydroxymethylurfural and furfural and furnish a raffinate containing a solvent capable of dissolving hydroxymethylurfural and furfural to be utilized for extraction.

6. The method of claim 5 wherein the evaporation is accomplished with a multiple-effect evaporator.

7. The method of claim 1 wherein said aqueous acidic solution contains sulfuric acid.

8. The method of claim 1 wherein said lignocellulose solids are selected from the group consisting of wood, waste paper and municipal solid waste including an individual or a combination including an individual or a combination thereof.

9. The method of claim 1 wherein said aqueous acidic solution is subjected to temperature control to maintain boiling of said aqueous acidic solution.

10. The method of claim 1 wherein said solids, remaining from hydrolysis, removed from the vessel are subjected to filtration to produce filtered solids and a filtrate containing aqueous acidic solution.

11. The method of claim 10 wherein said filtrate containing aqueous acidic solution is recycled to said vessel.

12. The method of claim 10 wherein the previously filtered solids are subjected to extraction by water to produce extracted solids substantially free of aqueous acidic solution and an extractate containing extracted aqueous acidic solution.

13. The method of claim 12 wherein said extractate, containing extracted aqueous acidic solution, is combined with removed aqueous acidic solution.

14. The method of claim 13 wherein the combination of the extractate and removed aqueous acidic solution is subjected to humidification by air to remove water from the combination.

15. The method of claim 1 wherein said aqueous acidic solution is established and maintained at the boiling point of the aqueous acidic solution regardless of the pressure gradient within the vessel.

16. The method of claim 1 wherein said vessel is about twenty to about sixty feet in length to establish a temperature and pressure gradient within the vessel.

17. The method of claim 1 wherein said hydroxymethylurfural and the furfural are vaporized and removed from said vessel as vapor.

* * * * *